(12) United States Patent
Herrema et al.

(10) Patent No.: US 10,473,246 B2
(45) Date of Patent: Nov. 12, 2019

(54) CONNECTOR FOR A FLUID HANDLING SYSTEM

(71) Applicant: Flow-Rite Controls, Ltd., Byron Center, MI (US)

(72) Inventors: Mark W. Herrema, Rockford, MI (US); Daniel N. Campau, Ada, MI (US); Scott T. Kloote, Coopersville, MI (US); Dennis J. Anderson, Coopersville, MI (US)

(73) Assignee: FLOW-RITE CONTROLS, LTD., Byron Center, MI (US)

( * ) Notice: Subject to any disclaimer, the term of this patent is extended or adjusted under 35 U.S.C. 154(b) by 211 days.

(21) Appl. No.: 15/692,590

(22) Filed: Aug. 31, 2017

(65) Prior Publication Data

US 2019/0063652 A1 Feb. 28, 2019

(51) Int. Cl.
| | |
|---|---|
| *F16L 37/088* | (2006.01) |
| *F16L 37/138* | (2006.01) |
| *F16L 37/127* | (2006.01) |
| *A61M 39/10* | (2006.01) |

(52) U.S. Cl.
CPC .......... *F16L 37/088* (2013.01); *F16L 37/127* (2013.01); *F16L 37/138* (2013.01); *A61M 39/1011* (2013.01); *A61M 2039/1033* (2013.01)

(58) Field of Classification Search
CPC . F16L 29/00; F16L 29/02; F16L 29/04; F16L 37/0847; F16L 37/0842; F16L 37/088; F16L 37/10; F16L 37/101; F16L 37/12; F16L 37/1205; F16L 37/127

USPC ........................ 285/35, 34, 82, 84, 314, 315
See application file for complete search history.

(56) References Cited

U.S. PATENT DOCUMENTS

| | | | | |
|---|---|---|---|---|
| 2,259,137 A | * | 10/1941 | Iftiger, Sr. ........... | F16L 37/1215 285/35 |
| 2,327,714 A | * | 8/1943 | Iftiger, Sr. ........... | F16L 37/1215 285/315 |
| 3,870,332 A | * | 3/1975 | Eaton .................. | F16L 37/1215 285/322 |
| 4,191,406 A | * | 3/1980 | Eaton ................... | F16L 37/121 285/315 |
| 4,557,508 A | * | 12/1985 | Walker ................. | E21B 33/038 285/84 |
| 4,706,847 A | * | 11/1987 | Sankey .................... | B67D 1/04 137/329.4 |
| 5,265,917 A | * | 11/1993 | Hitz ....................... | F16L 37/138 285/315 |
| 5,348,048 A | * | 9/1994 | Schirado .............. | B67D 1/1256 137/588 |

(Continued)

*Primary Examiner* — Aaron M Dunwoody
(74) *Attorney, Agent, or Firm* — Warner Norcross and Judd LLP

(57) ABSTRACT

The specification discloses a marine fluid connection system including a fitting and a connector. The fitting is cylindrical and includes a radially extending flange. The connector includes a cylindrical body, a plurality of levers on the body, and a locking ring on the body. The levers are movable between a latched position, in which the levers are closed on the flange to lock the connector on the fitting, and an unlatched position, in which the levers are open so that the connector may be removed from the fitting. The locking ring is axially movable with respect to the body to move the latches between their latched and unlatched positions.

14 Claims, 9 Drawing Sheets

(56) References Cited

U.S. PATENT DOCUMENTS

| | | | |
|---|---|---|---|
| 5,580,099 A * | 12/1996 | Eaton | F16L 37/0842 |
| | | | 285/322 |
| 5,800,108 A * | 9/1998 | Cabahug | F16B 37/0857 |
| | | | 411/433 |
| 6,257,626 B1 | 7/2001 | Campau | |
| 6,443,496 B2 | 9/2002 | Campau | |
| 6,834,888 B2 | 12/2004 | Campau | |
| 8,297,658 B2 * | 10/2012 | Le Quere | F16L 37/1215 |
| | | | 285/307 |
| 8,317,234 B2 * | 11/2012 | McKay | E21B 33/038 |
| | | | 285/81 |
| 2004/0000788 A1 * | 1/2004 | Cronley | F16L 37/1215 |
| | | | 285/34 |
| 2004/0164547 A1 * | 8/2004 | Cronley | F16L 37/1215 |
| | | | 285/34 |
| 2010/0244435 A1 * | 9/2010 | Stroope | F16L 37/1215 |
| | | | 285/34 |
| 2010/0327575 A1 * | 12/2010 | Blanchard | F16L 37/1215 |
| | | | 285/34 |
| 2011/0062703 A1 * | 3/2011 | Lopez | A61J 1/2096 |
| | | | 285/129.1 |
| 2016/0102796 A1 * | 4/2016 | Ciccone | A61M 39/10 |
| | | | 251/148 |

\* cited by examiner

CONNECTOR FOR A FLUID HANDLING SYSTEM

BACKGROUND OF THE INVENTION

The present invention relates to fluid handling systems, and more particularly to connectors for fluid handling systems.

It is common practice in the fluid handling industry to use a "quick connect" system for attaching hoses to fittings, particularly in marine applications such as through-hulls, bulkheads, and soft-walled bags. Exemplary connectors are illustrated in U.S. Pat. No. 6,834,888 to Campau; U.S. Pat. No. 6,443,496 to Campau; and U.S. Pat. No. 6,257,626 to Campau. These connectors have become popular in the marine industry for handling fluids in livewells, wakeboarding ballast systems, and bilge pump systems. These connectors typically include integral locking levers joined to the connector body both at the base of each lever and at the fulcrum of each lever.

This design is relatively simple, reducing the number of components, but also has its disadvantages. Because the connector body and the levers are integral with one another, the connector body and the levers must be fabricated of the same material. Therefore, material selection must be a compromise between strength and ductility. Because the integral levers must deflect regularly during connection and disconnection, appropriate materials are limited to those having relatively high ductility. Therefore, the material selection cannot be optimized for the strength of the connection joint.

SUMMARY OF THE INVENTION

The present invention provides an improved connector for a fluid handling system. The connector includes a body, a plurality of levers, and a locking ring. The levers and the locking ring are supported on the body. The levers are movable between a latched position, in which the connector is latched onto a fitting, and an unlatched position, in which the connector may be installed on or removed from the fitting. The locking ring is movable with respect to the connector to move the levers between their latched position and their unlatched position.

The body, the levers, and the locking ring are separate and/or or independent of one another. Therefore each component may be fabricated of a material selected, and preferably optimized, for the function of that component.

In one embodiment, the body defines a plurality of cradles, and each lever includes a pivot in one of the cradles. The locking ring includes a cam that interfaces with the levers to move the levers between the latched and unlatched positions.

These and other advantages and features of the invention will be more fully understood and appreciated by reference to the description of the current embodiment and the drawings.

DESCRIPTION OF THE CURRENT EMBODIMENT

Figure 1:
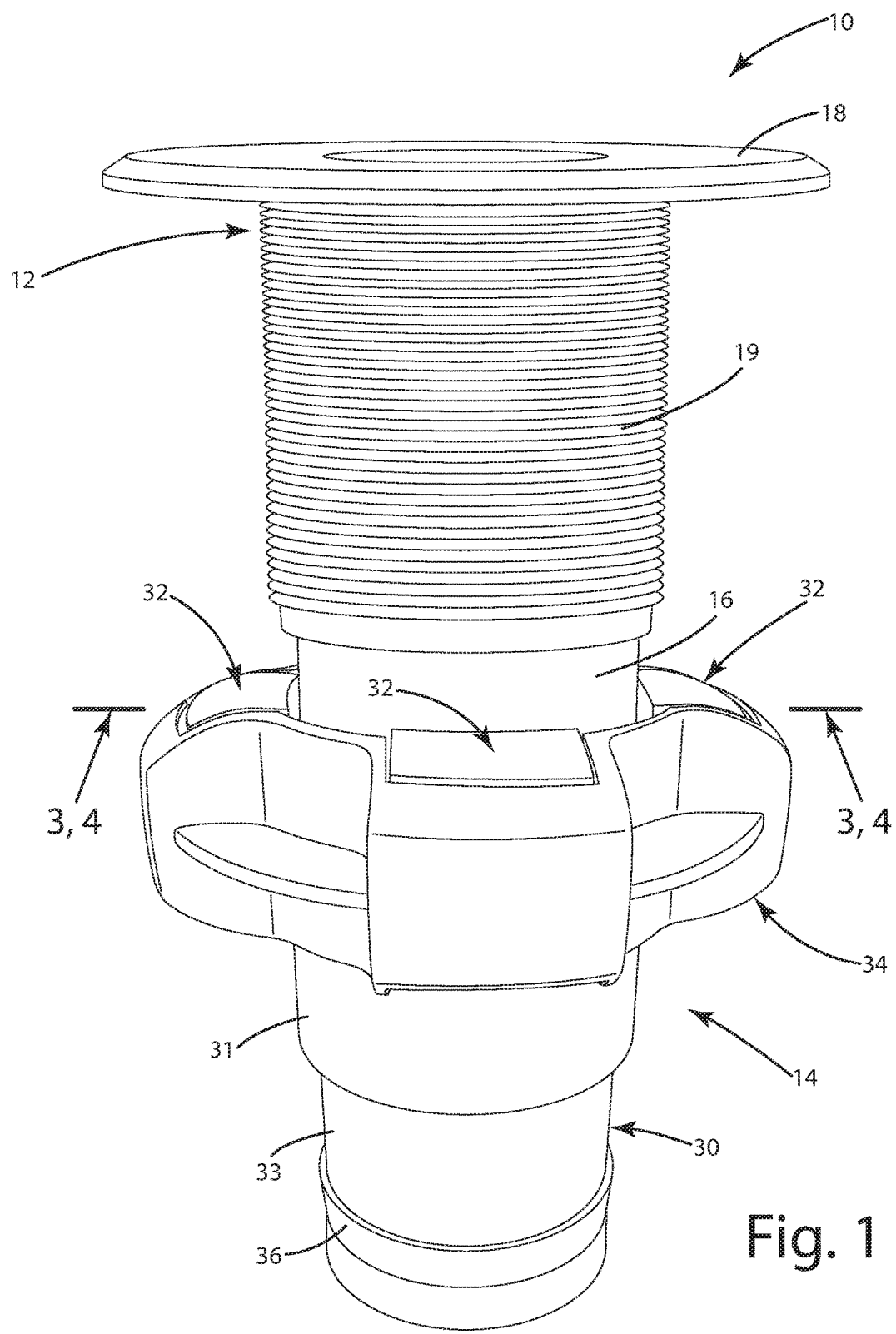
FIG. 1 is a perspective view of the fluid connection system.
Figure 2:
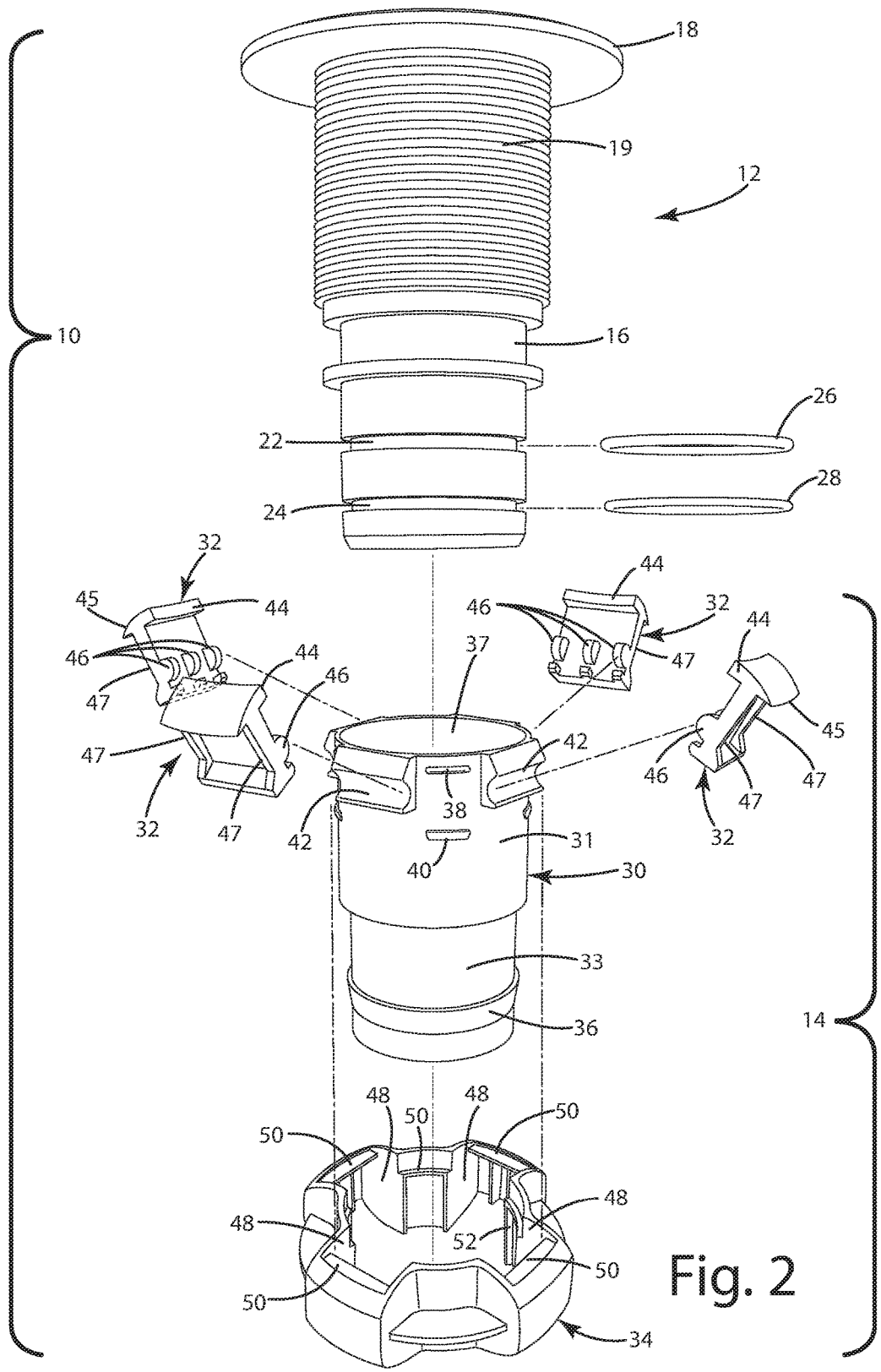
FIG. 2 is a perspective exploded view of the fluid connection system.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and practiced or being carried out in alternative ways not expressly disclosed herein. Also, it is to be understood that the phraseology and terminology used herein are for the purpose of description and should not be regarded as limiting. The use of "including" and "comprising" and variations thereof is intended to encompass the items listed thereafter and equivalents thereof as well as additional items and equivalents thereof.

Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

Directional terms, such as "vertical," "horizontal," "top," "bottom," "upper," "lower," "inner," "inwardly," "outer" and "outwardly," are used to assist in describing the invention based on the orientation of the embodiments shown in the drawings. The use of directional terms should not be interpreted to limit the invention to any specific orientation(s).

I. First Embodiment

A fluid connection system in accordance with a first embodiment of the invention is illustrated in FIGS. 1-5 and designated 10. The fluid connection system includes a fitting 12 and a connector 14.

The fitting 12 is of a conventional design generally known to those skilled in the art. The fitting 12 may be a marine thru-hull fitting. The fitting 12 includes a cylindrical body 16 having a threaded portion 19 for receiving a connector (not shown) when the fitting is installed within a hull. The fitting alternatively may be a ballast bag fitting or a fitting for any other application now known or later developed. A mounting flange 18 and a locking flange 20 extend radially outwardly from the body 16. The body defines two grooves 22 and 24 in which O-rings 26 and 28 respectively are seated.

The connector 14 includes a body 30, a plurality of levers 32, and a locking ring 34. The levers 32 and the locking ring 34 are supported on the body 30 as will be described.

The body 30 is generally cylindrical and includes a first portion 31 and a second portion 33. The first portion 31 defines an open end 37. The inner and outer diameters of the first portion 31 are somewhat larger than the inner and outer diameters respectively of the second portion 33, resulting in a shoulder 35 at the junction of the two portions. Alternatively, the first and second portions 31 and 33 may have the same inner and outer diameters, in which case the shoulder 35 would not exist.

The first portion 31 includes a plurality of pairs of detents 38 and 40 extending radially outwardly from the first portion. In the first embodiment, four pairs of the detents 38 and 40 are provided about the circumference of the first portion 31 and are oriented approximately 90° from one another. The body 30 may include fewer or greater numbers of pairs of detents 38 and 40. The detents 40 assisting in limiting the travel of the locking ring 34 in the downward direction in the unlatched position, as will be described. The detents 38 assist in retaining the locking ring 34 in the latched position, again as will be described.

The first portion 31 includes a plurality of cradles or sockets 42. In the first embodiment, four of the cradles 42 are provided about the circumference of the first portion 31 and are oriented approximately 90° apart from one another. Each of the cradles 42 may be oriented 45° from both adjacent pairs of detents 38 and 40. The cradles 42 define a pivot or hinge point for the levers 32 as will be described.

The second portion 33 includes a radially extending, annular ring 36 of conventional design to facilitate the fluid-tight connection of a hose or other fluid conveyance element (not shown) to the second portion.

In the current embodiment, four levers 32 are provided—one for each of the cradles 42. Each lever 32 includes an inwardly oriented latch 44 and an opposite outwardly oriented stop 45. Each lever further includes a pivot or pivot portion 46, which comprises three equally spaced nubs. Alternative pivot structures are within the scope of the present invention. Each pivot portion 46 fits within and associated cradle 42. Consequently, each lever 32 may pivot about the pivot portion 46 within the cradle 42. Each lever 32 additionally includes one or more cam followers 47 generally opposite the pivot 46.

Figure 3:
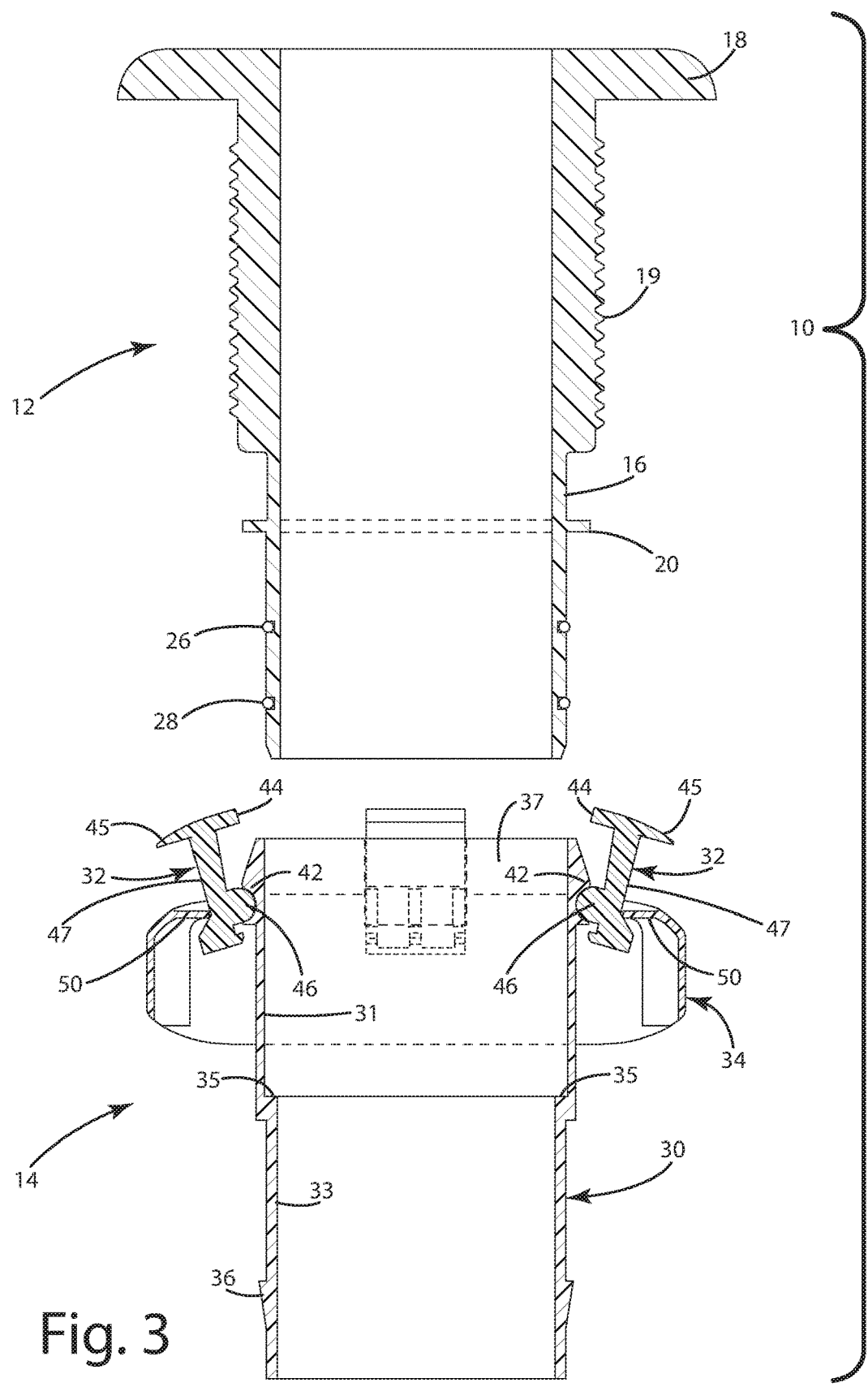
FIG. 3 is a sectional view of the fluid connection system, showing the connector separated from the fitting.
Figure 4:
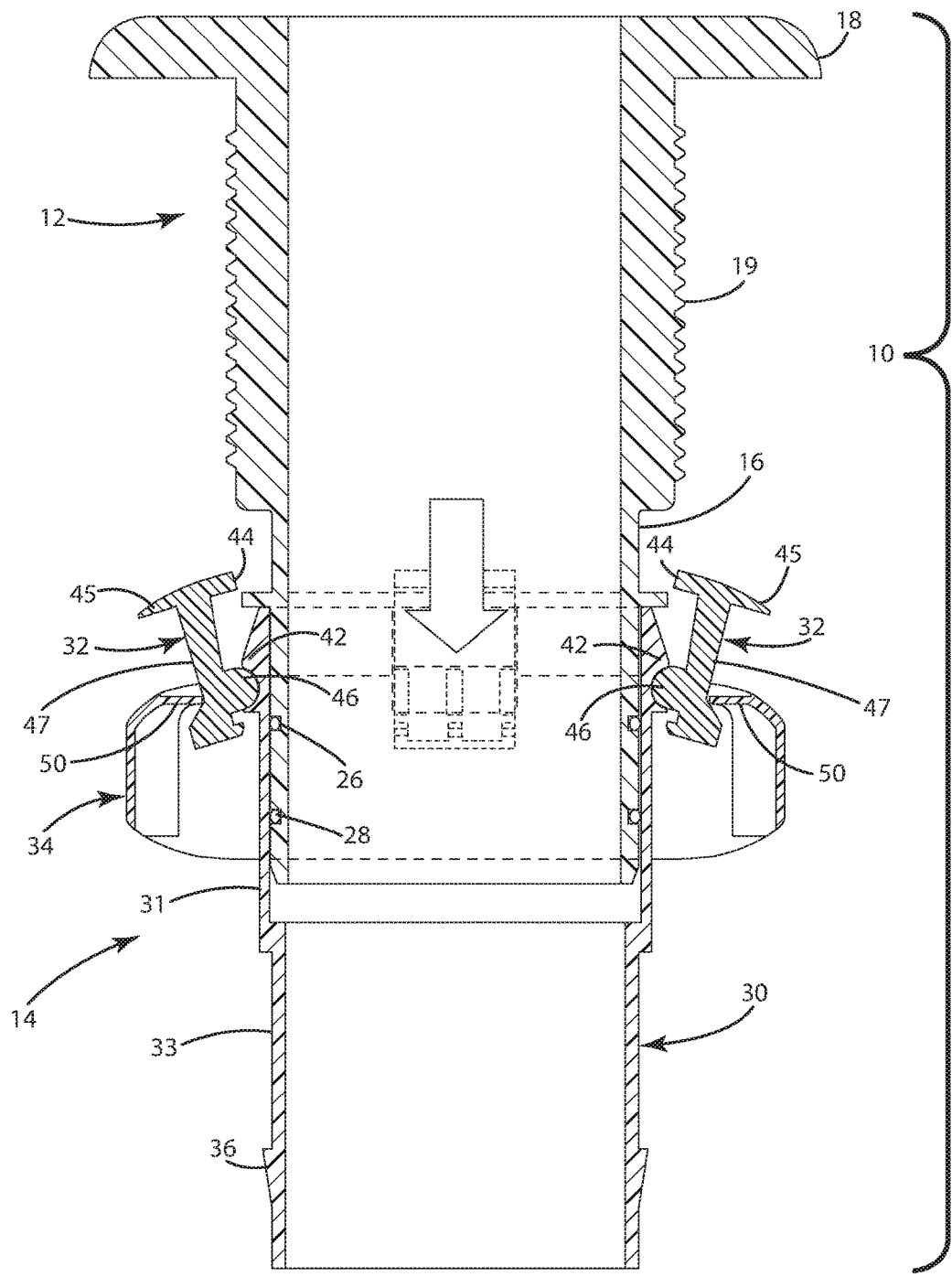
FIG. 4 is a sectional view similar to FIG. 3, showing the connector on the fitting and with the latches open.
Figure 5:
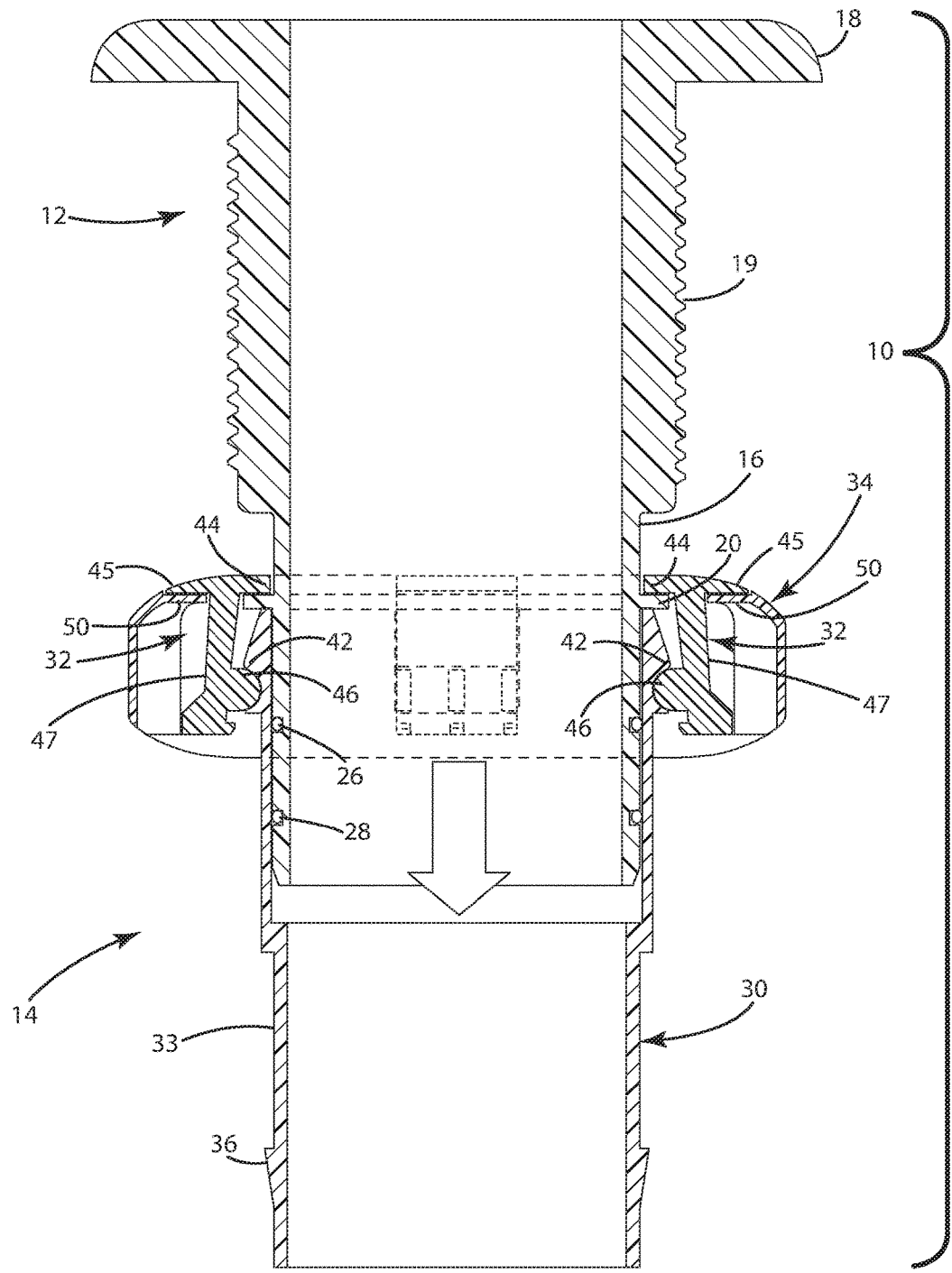
FIG. 5 is a sectional view similar to FIG. 4, showing the connector on the fitting and with the latches closed.
Figure 6:
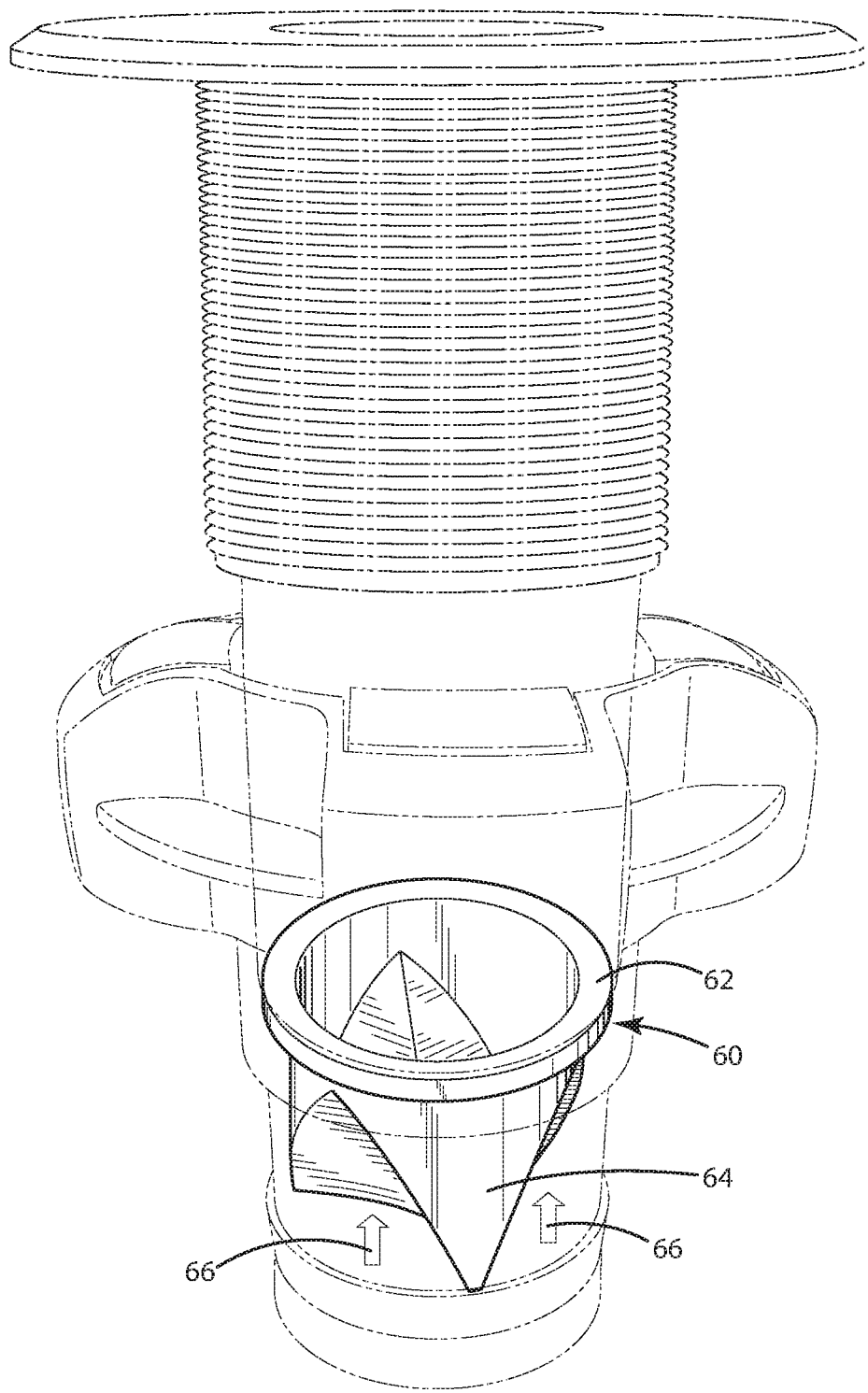
FIG. 6 is a perspective view similar to FIG. 1 showing the connector and the fitting in phantom and showing an optional check valve in the closed position.
Figure 7:
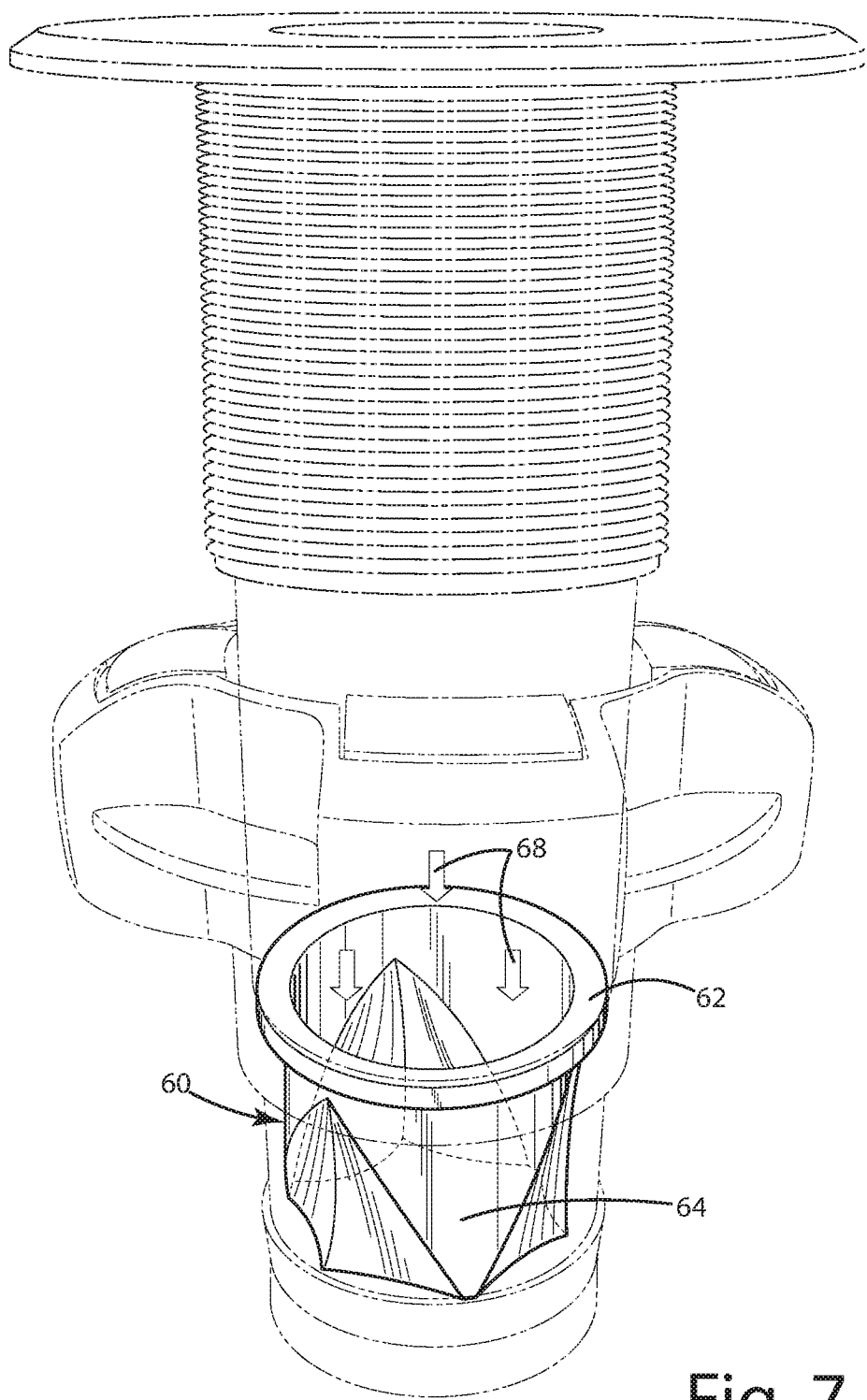
FIG. 7 is a perspective view similar to FIG. 6, showing the check valve in the open position.

The mounting ring 34 is supported on the body 30 for axial movement with respect to the body between an unlatched position illustrated in FIGS. 3-4 and a latched position illustrated in FIGS. 1 and 5.

The mounting ring 34 defines four inwardly facing lever pockets 48—one for each of the levers 32. In the first embodiment, the pockets are oriented approximately 90° apart from one another. A cam 50 extends into each pocket 48. Each cam 50 engages the cam follower 47 of the associated lever 32 and rides along the cam follower during movement of the locking ring 34 to move the levers 32 between latched and unlatched positions.

The mounting ring 34 includes a plurality of inwardly facing stops 52. Downward travel of the mounting ring 34 in the unlatched position is limited when stops 52 on the mounting ring engage the detents 40 on the body 30. Upward travel of the mounting ring 34 in the latched position is limited by the engagement of the cams 50 with the lever stops 45. The mounting ring 34 includes detents (not illustrated) that engage with the detents 38 to retain the mounting ring in the latched position.

The present invention enables the connector body 30 and the levers 32 to be fabricated of different materials. The material properties can be selected based on the application. In one embodiment, the levers 32 may be fabricated of a high-strength plastic such as glass-filled polypropylene or even metal; and the connector body 30 may be fabricated of a high-impact plastic such as polypropylene.

The operation of the connector 14 is perhaps best illustrated in FIGS. 3-5. Referring initially to FIG. 3, the connector 14 is shown separated from the fitting 12 with the mounting ring 34 in its unlatched position. The cams 50 engage the lower portion of each cam follower 47 to move or force the levers 32 into the unlatched or open position.

Referring next to FIG. 4, the connector 14 is shown installed on the fitting 12, but with the levers 32 still in their unlatched position. The body 30, and specifically the first portion 31, abuts and engages the locking flange 20 on the fitting 12. The latches 44 on the levers 32, when in the unlatched position, may clear the locking ring 20 as the connector 14 is installed on the fitting 12.

Referring next to FIG. 5, the connector 14 is shown installed and latched on the fitting 12. To close or latch the levers 32, the mounting ring 34 is moved upwardly or toward the mouth 37 of the connector 14. As the mounting ring 34 moves into the latched position, the cams 50 ride along the cam followers 47 to pivot, move, and/or force the levers 32 into the locked position. When in this position, the latches 44 are closed on the locking ring 20. Consequently, the connector 14 may not be removed from the fitting 12 until the latches are moved to the open or unlatched position.

The connector 14 may be easily unlatched and uninstalled using the reverse of the steps enumerated above in conjunction with installation and latching. Consequently, the connector 14 may be repeatedly installed and uninstalled, as well as latched and unlatched, on the fitting 12.

II. Second Embodiment

A fluid connection system in accordance with a second embodiment of the invention is illustrated in FIGS. 6-9. The fluid connection system of the second embodiment is identical to the fluid connection system of the first embodiment, with the exception that the second embodiment additionally includes an optional check valve 60. The previously described components (i.e. the fitting 12 and the connector 14) and their operation will not be re-described.

The valve 60 may be a duckbill valve or any other check valve of conventional design known to those skilled in the art. The illustrated duckbill valve is a one-piece, elastomeric component that acts as a backflow prevention device, a one-way valve, or a check valve. The valve includes a shoulder 62 and a plurality of lips 64. The valve 60 is shown closed in FIGS. 6 and 8-9. The closed position is the natural state of the valve 60, and the valve is forced more tightly into this position when positive fluid pressure is in the direction of the arrows 66 in FIG. 6. The valve 60 is shown open in FIG. 7. The open position is the non-natural state of the valve 60. The valve is forced open by fluid flow when in the direction of the arrows 68 in FIG. 7.

Figure 8:
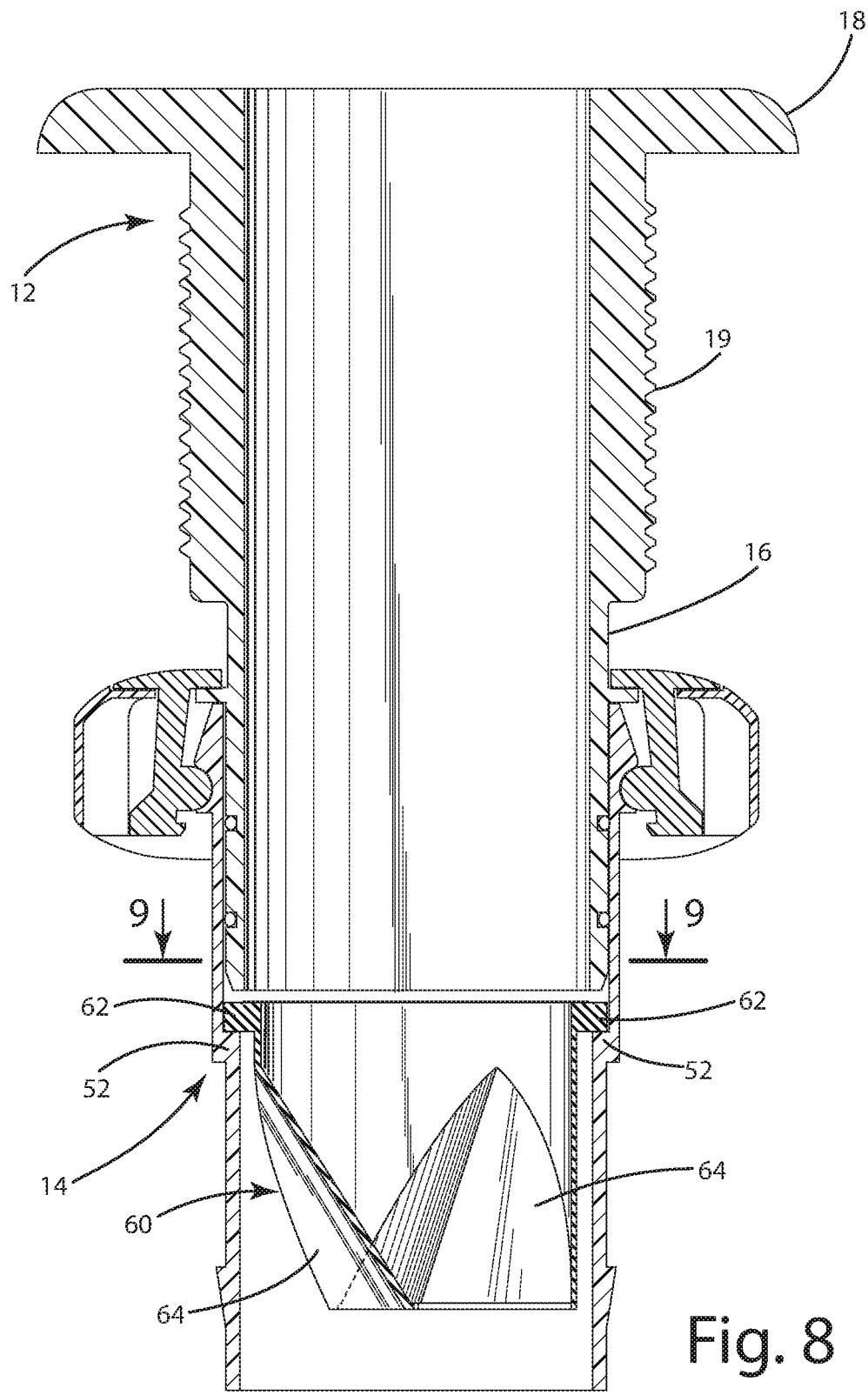
FIG. 8 is a sectional view similar to FIG. 5, and including the optional check valve.
Figure 9:
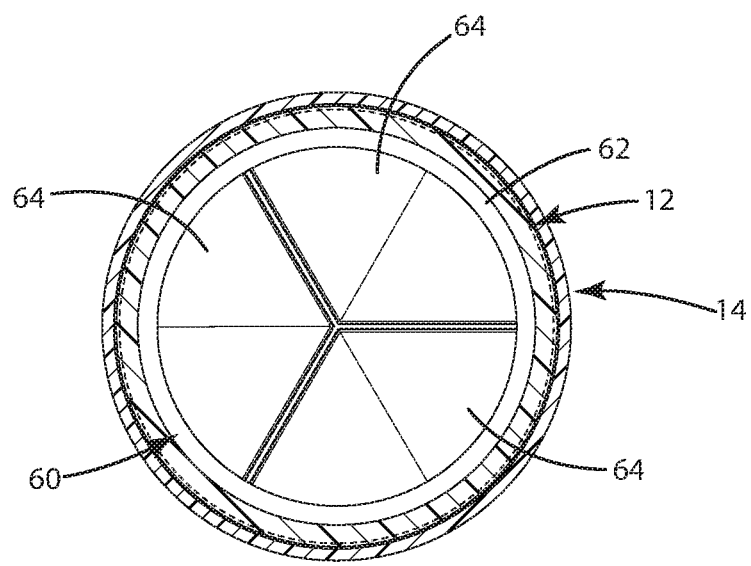
FIG. 9 is a sectional view taken along line 9-9 in FIG. 8.

The securement of the valve 60 within the connector 14 is perhaps best illustrated in FIG. 8. The shoulder 62 of the valve 60 is seated on the shoulder 52 of the body 30. The shoulder 62 of the valve is secured in position by a pinching action between the shoulder 52 and the fitting 12.

When installed, the valve 60 provides a simple, but highly effective, check valve function within the connector 14. This function is desirable, for example, in marine applications such as livewells, bilge pumps, and ballast bags.

Normally, a check valve is added as a separate component to a fluid handling system or as an addition to a threaded or barbed fitting. This invention enables a check valve to be integrated into the connector. This novel approach simplifies the overall fluid handling system by reducing the number of components and therefore the number of potential leak points.

The above descriptions are those of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "the," is not to be construed as limiting the element to the singular.

The embodiments of the invention in which an exclusive property or privilege is claimed are defined as follows:

1. A connector for a fluid handling system having a fitting including a radially extending flange, the connector comprising:
    a body adapted to fit on the fitting, the body defining a plurality of lever sockets, the body further defining an axis;
    a plurality of levers supported on the body, each of the levers including an inwardly oriented latch and an opposite outwardly oriented stop, the levers having a latched position in which the latches engage the flange when the body is fitted on the fitting, the latches have an unlatched position in which the latches are released from the flange, each of the levers including a pivot portion fitted within one of the sockets, the levers being movable about the pivot portions between the latched position and the unlatched position, each of the levers further including a cam follower opposite the pivot portion; and
    a locking ring supported on the body and movable axially with respect to the body, the locking ring engaging the levers to move the levers, the locking ring defining a plurality of inwardly facing lever pockets each receiving one of the levers, the locking ring including a plurality of cams each extending into one of the lever pockets and engaging the cam follower on one of the levers, the locking ring having a latched position in which the locking ring cams force the latches into their latched position, the locking ring have an unlatched position in which the locking ring cams force the latches into their unlatched position, the locking ring cams riding along the respective cam followers to pivot the levers between the latched and unlatched positions, the travel of the locking ring in the latched position is limited by the engagement of the locking ring cams with the lever stops.

2. A connector as defined in claim 1 wherein the body, the levers, and the locking ring are independent from one another.

3. A connector as defined in claim 2 wherein the lever material is different from the body material.

4. A connector as defined in claim 1 wherein the fluid handling system is a marine fluid handling system.

5. A connector as defined in claim 1 further comprising a check valve within the body.

6. A connector for a marine fluid handling system including a cylindrical fitting having a radially extending flange, the connector comprising:
    a cylindrical body adapted to fit on the fitting, the body defining a plurality of lever sockets the body further defining an axis;
    a plurality of levers independent of the body, each of the levers including a lever pivot fitted in one of the lever sockets, each of the levers including an inwardly oriented latch and an outwardly oriented stop, the levers having a latched position in which the latches engage the flange when the body is fitted on the fitting, the latches having an unlatched position in which the latches are released from the flange, the levers moving between the latched position and the unlatched position through pivoting motion about the lever pivots within the lever sockets each of the levers further including a cam follower opposite the pivot; and
    a locking ring supported on the body and movable axially with respect to the body, the locking ring engaging the levers to move the levers, the locking ring defining a plurality of inwardly facing lever pockets each receiving one of the levers, the locking ring including a plurality of cams each extending into one of the lever pockets and engaging the cam follower on one of the levers, the locking ring having a latched position in which the locking ring cams close the latches into their latched position, the locking ring have an unlatched position in which the locking ring cams open the latches into their unlatched position, the locking ring cams riding along the respective cam followers to pivot the levers between the latched and unlatched positions, the travel of the locking ring in the latched position is limited by the engagement of the locking ring cams with the lever stops.

7. A connector as defined in claim 6 wherein the body, the levers, and the locking ring are independent from one another.

8. A connector as defined in claim 7 wherein the lever material is different from the body material.

9. A connector as defined in claim 6 further comprising a check valve within the body.

10. A fluid connection system comprising:
    a fitting including a radially extending flange; and
    a connector releasably installable on the fitting, the connector including:
        a body adapted to fit on the fitting, the body defining a plurality of lever sockets, the body further defining an axis;
        a plurality of levers supported on the body, each of the levers including an inwardly oriented latch and an opposite outwardly oriented stop, the levers having a latched position in which the latches engage the flange when the body is fitted on the fitting, the latches have an unlatched position in which the latches are released from the flange, each of the levers including a pivot portion fitted within one of the lever sockets, the levers being movable about the pivot portions between the latched position and the unlatched position, each of the levers including a cam follower opposite the pivot portion; and a locking ring supported on the body and movable axially with respect to the body, the locking ring engaging the levers to move the levers, the locking ring defining a plurality of inwardly facing lever pockets each receiving one of the levers, the locking ring including a plurality of cams each extending into one of the lever pockets and engaging the cam follower on one of the levers, the locking ring having a latched position in which the locking ring cams force the latches into their latched position, the locking ring have an unlatched position in which the locking ring cams force the latches into their unlatched position, the locking ring cams riding along the respective cam followers to pivot the levers between the latched and unlatched positions, the travel of the locking ring in the latched position is limited by the engagement of the locking ring cams with the lever stops.

11. A fluid connection system as defined in claim 10 wherein the body, the levers, and the locking ring are independent from one another.

12. A connector as defined in claim 11 wherein the lever material is different from the body material.

13. A fluid connection system as defined in claim 10 wherein the fluid handling system is a marine fluid handling system.

14. A fluid connection system as defined in claim 10 further comprising a check valve within the body.

* * * * *

UNITED STATES PATENT AND TRADEMARK OFFICE
CERTIFICATE OF CORRECTION

PATENT NO. : 10,473,246 B2
APPLICATION NO. : 15/692590
DATED : November 12, 2019
INVENTOR(S) : Mark W. Herrema et al.

Page 1 of 1

It is certified that error appears in the above-identified patent and that said Letters Patent is hereby corrected as shown below:

In the Claims

Column 6, Claim 6, Line 17:
"lever sockets the body"
Should be:
-- lever sockets, the body --

Column 6, Claim 6, Line 29:
"lever sockets the body"
Should be:
-- lever sockets, the body --

Signed and Sealed this
Fourth Day of February, 2020

Andrei Iancu
*Director of the United States Patent and Trademark Office*